(12) United States Patent
Shlomovitz et al.

(10) Patent No.: US 11,389,629 B2
(45) Date of Patent: Jul. 19, 2022

(54) SYSTEMS AND METHODS FOR PERCUTANEOUS BODY LUMEN DRAINAGE

(71) Applicant: Boston Scientific Scimed, Inc., Maple Grove, MN (US)

(72) Inventors: Eran Shlomovitz, Toronto (CA); Peter L. Dayton, Brookline, MA (US); Katharine Eckerline, Boston, MA (US); Bryan Bannon, Duxbury, MA (US); Barry Weitzner, Acton, MA (US); Thomas DeSimio, Alpine, CA (US); Lee Swanstrom, Portland, OR (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 1016 days.

(21) Appl. No.: 15/944,185

(22) Filed: Apr. 3, 2018

(65) Prior Publication Data
US 2018/0280669 A1 Oct. 4, 2018

Related U.S. Application Data

(60) Provisional application No. 62/481,621, filed on Apr. 4, 2017.

(51) Int. Cl.
| | | |
|---|---|---|
| *A61M 27/00* | (2006.01) |
| *A61B 17/00* | (2006.01) |
| *A61B 17/11* | (2006.01) |
| *A61F 2/04* | (2013.01) |
| *A61B 90/00* | (2016.01) |
| *A61F 2/848* | (2013.01) |
| *A61M 5/32* | (2006.01) |
| *A61M 1/00* | (2006.01) |
| *A61B 34/20* | (2016.01) |
| *A61B 17/34* | (2006.01) |

(52) U.S. Cl.
CPC .......... *A61M 27/002* (2013.01); *A61B 17/00* (2013.01); *A61B 17/1114* (2013.01); *A61B 90/37* (2016.02); *A61F 2/04* (2013.01); *A61F 2/848* (2013.01); *A61B 34/20* (2016.02); *A61B 2017/1139* (2013.01); *A61B 2017/3413* (2013.01); *A61B 2090/376* (2016.02); *A61B 2090/378* (2016.02); *A61F 2002/041* (2013.01)

(58) Field of Classification Search
CPC combination set(s) only.
See application file for complete search history.

(56) References Cited

U.S. PATENT DOCUMENTS

| | | | | |
|---|---|---|---|---|
| 6,989,003 | B2 * | 1/2006 | Wing ................ | A61B 17/34 604/161 |
| 10,321,910 | B2 * | 6/2019 | Phan ................ | A61F 2/966 |
| 10,471,236 | B2 * | 11/2019 | Rosenberg ........ | A61M 25/04 |
| 2015/0126906 | A1 * | 5/2015 | Kalloo .............. | A61M 25/09 600/585 |

* cited by examiner

*Primary Examiner* — Tatyana Zalukaeva
*Assistant Examiner* — Ilya Y Treyger
(74) *Attorney, Agent, or Firm* — Seager, Tufte & Wickhem, LLP (57) ABSTRACT

The present disclosure relates generally to the field of devices and procedures for placement of a medical device between adjacent tissue structures. In particular, the present disclosure relates to systems and methods for percutaneous placement of a drainage stent between the gallbladder and gastric lumen (e.g., cholecystogastrostomy), or gallbladder and duodenum (cholecystoduodenostomy).

20 Claims, 7 Drawing Sheets

SYSTEMS AND METHODS FOR PERCUTANEOUS BODY LUMEN DRAINAGE

CROSS REFERENCE TO RELATED APPLICATIONS

This application claims the benefit of priority under 35 U.S.C. § 119 to U.S. Provisional Patent Application Ser. No. 62/481,621, filed on Apr. 4, 2017, which is incorporated by reference in its entirety for all purposes.

FIELD

The present disclosure relates generally to the field of medical devices and establishing fluid communication between body lumens. In particular, the present disclosure relates to systems and methods for percutaneous placement of a medical device between lumen structures, such as a stent between the gallbladder and the stomach or duodenum to facilitate drainage therebetween.

BACKGROUND

The desire to establish access to body lumens to create fluid communication from one to the other is present under various circumstances and conditions, such as the desire to establish access from a diseased body lumen to another body lumen to facilitate drainage as an alternative to draining the diseased body lumen along a path to a location external of a patient's body.

As an example, inflammation of the gallbladder (e.g., cholecystitis) is typically caused by gallstones that block the release of bile into the digestive system, and may result in episodic or continual discomfort to the patient. Although a preferred treatment for cholecystitis is surgical removal of the gallbladder (e.g., cholecystectomy), patients who are poorly suited for open or laparoscopic surgical intervention may require an alternative interventional radiology (IR) procedure to drain the gallbladder. An exemplary IR procedure involves draining the gallbladder outside the body (e.g., collection bag, etc.) through a percutaneously implanted tube. Although this procedure is relatively straightforward and widely accessible, the external drain tends to be uncomfortable and may become dislodged and/or infected, requiring additional surgical intervention and possibly leading to formation of a permanent fistula. Endoscopic (e.g., transmural or transpapillary) gallbladder drainage procedures may address some of the problems associated with external drainage tubes. However, institutions may lack the necessary medical equipment and/or trained personnel required to perform such procedures, e.g., endoscopic ultrasound (EUS) procedures.

A variety of advantageous medical outcomes may therefore be realized by the systems and/or methods of the present disclosure, which allow the percutaneous placement of a medical device between body lumen structures.

SUMMARY

In one aspect, the present disclosure relates to a method comprising advancing a hollow needle percutaneously through a second body lumen and a tissue wall of a first body lumen, such that a distal end of the needle is disposed within the first body lumen, advancing a guidewire through the needle into the first body lumen, removing the needle from over the guidewire, advancing a delivery system for a stent loaded thereon over the guidewire such that a distal end of the delivery system is disposed within the first body lumen and deploying the stent from the delivery system to establish fluid communication between the first body lumen and the second body lumen. In addition, or alternatively, a sheath may be advanced over the guidewire such that a distal end of the sheath is disposed within the first body lumen. The delivery system may be loaded over the guidewire and through the sheath. The hollow needle may include a trocar with a sharpened tip and an obturator (or stylet) inserted therethrough. The obturator may be removed from the trocar prior to advancing the guidewire through the trocar. The delivery system may include an inner member with a lumen therethrough to receive the guidewire, and an outer member disposed coaxially about the inner member, whereby the stent may be loaded on the delivery system between the inner member and the outer member. The deploying step may include exposing a distal portion of the stent from within the delivery system, such that the distal portion forms a distal flange of the stent within the first body lumen. The deploying step may further include retracting the delivery system to place the distal flange of the stent in contact with an inner surface of the tissue wall. The deploying step may further include retracting the delivery system such that the distal end of the delivery system is disposed within the second body lumen. The deploying step may further include exposing a proximal portion of the stent from within the delivery system, such that the proximal portion forms a proximal flange of the stent within the second body lumen. The needle may be advanced through a portion of the liver prior to the second body lumen. The needle may be advanced through a portion of the peritoneal cavity prior to the second body lumen. The needle may be advanced through a body lumen that is not the first or second body lumen prior to being advanced through the second body lumen. The second body lumen may be the gallbladder. The tissue wall may be the gastric wall and the first body lumen may be the stomach. The tissue wall may be the duodenal wall and the first body lumen may be the duodenum. The tissue wall may be the jejunum wall and the first body lumen may be the jejunum. The second body lumen may be the stomach. The tissue wall may be the duodenal wall and the first body lumen may be the duodenum. The tissue wall may be the jejunum wall and the first body lumen may be the jejunum. The tissue wall may be the ileum wall and the first body lumen may be the ileum. The second body lumen may be the common biliary duct (CBD), the tissue wall may be the duodenal wall and the first body lumen may be the duodenum. The second body lumen may be a portion of the intestine, the tissue wall may be the wall of a second portion of intestine and the first body lumen may be the second portion of intestine. The second body lumen may be a pseudocyst or an abscess, and the tissue wall and the first body lumen may be the duodenal wall and duodenum or the gastric wall and stomach. Each step of the method may be performed under at least ultrasonic guidance. Each step of the method may be performed under at least fluoroscopic guidance. Each step of the method may be performed under ultrasonic guidance and fluoroscopic guidance. The steps of the method may be performed laparoscopically.

In another aspect, the present disclosure relates to a method comprising advancing a needle percutaneously to establish an access path through a second body lumen and a tissue wall of a first body lumen, such that a distal end of the needle reaches an interior of a first body lumen, advancing a guidewire along the access path to the first body lumen interior, advancing a delivery system for a stent having distal and proximal flanges over the guidewire to the first body lumen interior and delivering the stent from the delivery system, such that the distal flange of the stent is deployed in the interior of the first body lumen and the proximal flange of the stent is deployed in the second body lumen. The distal flange may engage a distal face of the tissue wall and the proximal flange may engage an interior wall of the second body lumen. After the delivery step, the first and second body lumens may be apposed and in fluid communication with each other. After the delivery step, drainage may be established through the stent from the second body lumen to the first body lumen. In addition to drainage, the communications may connect structures to allow passage of a variety of materials from one to the other, including but not limited to stones, food, passage of medical devices into difficult to reach regions of the body. The stent may include a covering around and along the stent between the proximal and distal flanges. The second body lumen may be the gallbladder. The tissue wall may be the gastric wall and the first body lumen may be the stomach. The tissue wall may be the duodenal wall and the first body lumen may be the duodenum. The tissue wall may be the jejunum wall and the first body lumen may be the jejunum. The second body lumen may be the stomach. The tissue wall may be the duodenal wall and the first body lumen may be the duodenum. The tissue wall may be the jejunum wall and the first body lumen may be the jejunum. The tissue wall may be the ileum wall and the first body lumen may be the ileum. The second body lumen may be the common biliary duct (CBD), the tissue wall may be the duodenal wall and the first body lumen may be the duodenum. The second body lumen may be a portion of the intestine, the tissue wall may be the wall of a second portion of intestine and the first body lumen may be the second portion of intestine. The second body lumen may be a pseudocyst or an abscess, and the tissue wall and the first body lumen may be the duodenal wall and duodenum or the gastric wall and stomach. Each step of the method may be performed under at least ultrasonic guidance. Each step of the method may be performed under at least fluoroscopic guidance. The method may be performed under ultrasonic guidance and fluoroscopic guidance. The steps of the method may be performed laparoscopically.

In yet another aspect, the present disclosure relates to a method comprising establishing a percutaneous path of access to a first body lumen through a second body lumen, delivering a stent having distal and proximal flanges (when expanded) along the path to the first body lumen, deploying the distal flange of the stent against a wall of the first body lumen within the first body lumen, pulling the distal flange back along the path to hold the wall of the first body lumen in apposition to a wall of the second body lumen and deploying the proximal flange of the stent against the wall of the second body lumen within the second body lumen. After the stent is fully deployed, drainage may be established through the stent from the second body lumen to the first body lumen. In addition to drainage, the communications may connect structures to allow passage of a variety of materials from one to the other, including but not limited to stones, food, passage of medical devices into difficult to reach regions of the body. The first body lumen may be the stomach or duodenum and the second body lumen may the gallbladder. The percutaneous path may pass through a portion of the liver prior to the second body lumen. The percutaneous access path may be established by advancing a needle directly through a skin layer. The stent may include a covering around and along the stent between the proximal and distal flanges. The second body lumen may be the gallbladder. The tissue wall may be the gastric wall and the first body lumen may be the stomach. The tissue wall may be the duodenal wall and the first body lumen may be the duodenum. The tissue wall may be the jejunum wall and the first body lumen may be the jejunum. The second body lumen may be the stomach, the tissue wall may be the duodenal wall and the first body lumen may be the duodenum. The tissue wall may be the jejunum wall and the first body lumen may be the jejunum. The tissue wall may be the ileum wall and the first body lumen may be the ileum. The second body lumen may be the common biliary duct (CBD), the tissue wall may be the duodenal wall and the first body lumen may be the duodenum. The second body lumen may be a portion of the intestine, the tissue wall may be the wall of a second portion of intestine and the first body lumen may be the second portion of intestine. The second body lumen may be a pseudocyst or an abscess, and the tissue wall and the first body lumen may be the duodenal wall and duodenum or the gastric wall and stomach. Each step of the method may be performed under at least ultrasonic guidance. Each step of the method may be performed under at least fluoroscopic guidance. The method may be performed under ultrasonic guidance and fluoroscopic guidance. The steps of the method may be performed laparoscopically.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures.

DETAILED DESCRIPTION

The present disclosure is not limited to the particular embodiments described herein. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

Although embodiments of the present disclosure are described with specific reference to systems and methods for placing a drainage stent between the gallbladder and the stomach (e.g., cholecystogastrostomy) or duodenum (e.g., cholecystoduodenostomy) without EUS guidance, it should be appreciated that such systems and methods may be used in a variety of medical procedures (e.g., external biliary drain conversion, enteroenterostomy, gastrojejunostomy, gastroduodenostomy and gastroileostomy, etc.) to establish and/or maintain a temporary or permanent open flow passage between a variety of body organs, lumens and spaces (e.g., the dermis, bladder, kidneys, walled-off pancreatic necrosis (WOPN), pseudocysts, abscesses, etc.) using a variety of imaging modalities. Moreover, the medical devices disclosed herein are not limited to drainage stents, but may include medical devices configured to facilitate access to organs or lumens for other purposes, such as removing obstruction and delivering therapy, including non-invasive manipulation of the tissue within the organ or lumen and/or the introduction of pharmacological agents via the open flow passage.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

As used herein, the term "distal" refers to the end farthest away from the medical professional when introducing a device into a patient, while the term "proximal" refers to the end closest to the medical professional when introducing a device into a patient.

In various embodiments, the present disclosure relates to a percutaneous method for creating an open flow passage between two or more structures (e.g., a first body lumen and a second body lumen). Percutaneous can include access directly through a skin layer or laparoscopically through a port. The procedures may be performed with ultrasound guidance, e.g., transabdominal ultrasound, or fluoroscopic guidance or some combination of the two.

Figure 1:
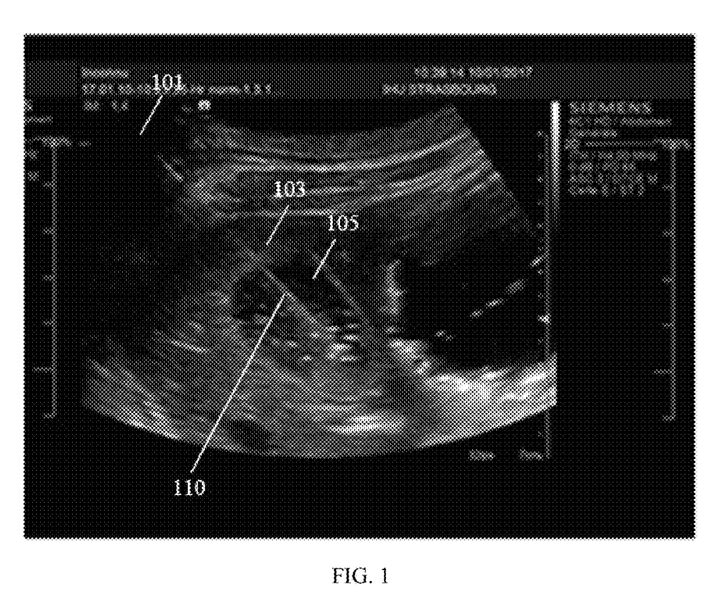
FIGS. 1, 2A, 2B, 3-5, 6A, 6B, and 7 illustrate exemplary steps for percutaneous placement of a medical device, according to embodiments of the present disclosure.

Referring to FIG. 1, in a first step of a percutaneous method according to the present disclosure, the patient may be placed on an operating table in a supine position, and the table tilted to place the gastric antrum in a dependent position. Alternatively, the patient may be placed in a position other than supine, e.g., on their left or right side. An appropriate volume of saline (e.g., approximately 500 cc) may then be introduced into the stomach, e.g., through a nasogastric tube, to remove open spaces or air pockets that might attenuate propagation of ultrasound energy. An 18-gauge hollow needle 110 (e.g., trocar with obturator, or needle with stylet) may then be percutaneously advanced under ultrasound guidance through a dermal layer (e.g., skin) 101 and a section of the liver parenchyma 103 into the gallbladder 105 (e.g., second body lumen). The liver parenchyma at the needle puncture site may preferably include a thickness of about 0.50 cm to about 2.00 cm to prevent deflation of the adjacent gallbladder upon penetration by the needle. In addition to supporting the punctured gallbladder, the spongy consistency of the liver parenchyma may provide a seal around the needle 110 to prevent leakage of the gallbladder contents into the pleural space.

Figure 2A:
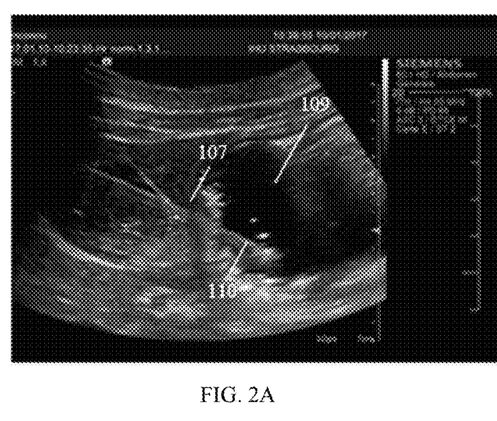
Figure 2B:
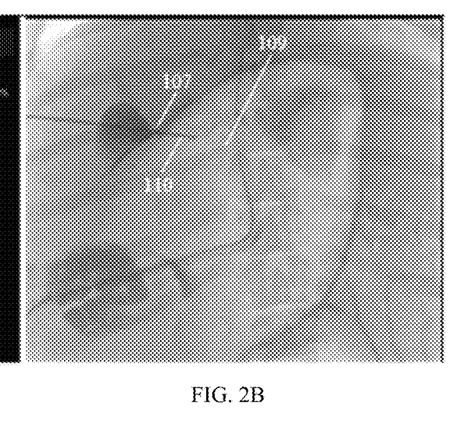

Referring to FIGS. 2A and 2B, the needle 110 may be further advanced through the gastric wall 107 (e.g., first tissue wall) and into the stomach 109 (e.g., first body lumen) under ultrasound (FIG. 2A) and/or fluoroscopic (FIG. 2B) guidance. In various embodiments, the needle 110 may be advanced through the second body lumen, first tissue wall and first body lumen without penetrating any portion of the liver.

Figure 3:
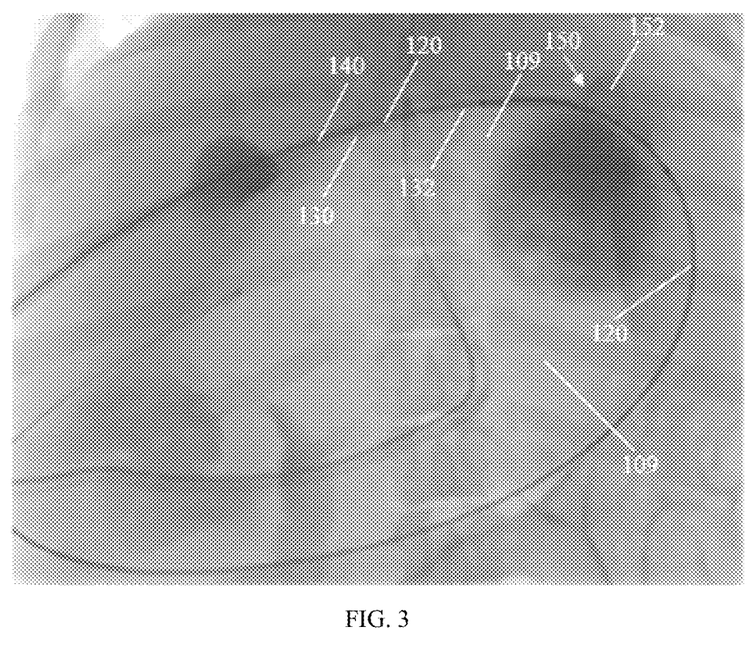

Referring to FIG. 3, the trocar obturator or stylet (not shown), when disposed within the hollow needle, may then be removed from the needle and a guidewire 120 advanced through the hollow needle into the stomach 109 under fluoroscopic guidance. A sufficient amount of the guidewire 120 may be advanced through the hollow needle to form a loop within the stomach 109 to maintain the proper location of the guidewire 120 throughout the medical procedure. The hollow needle may then be retracted over the guidewire 120, and a sheath 130 (e.g., 12-French) advanced over the guidewire 120 under fluoroscopic guidance to position a distal end 132 of the sheath within the stomach 109. A stent delivery system 140 may then be advanced over the guidewire 120 through the sheath 130 under fluoroscopic (FIG. 3) and/or ultrasonic (not shown) guidance such that a distal end of the stent delivery system 140 is positioned within the stomach 109. The stent delivery system 140 may include an inner member with a lumen extending therethrough to receive the guidewire 120, and an outer member disposed coaxially around the inner member. A drainage stent 150 may be loaded on the stent delivery system 140 in a collapsed or non-expanded configuration between the inner and outer member. A distal portion of the drainage stent 150 may be exposed from within the stent delivery system 140, such that the distal portion forms a distal flange 152 of the stent 150 within the stomach 109. In various embodiments, the stent delivery system may be advanced over the guidewire in the absence of a sheath.

Figure 4:
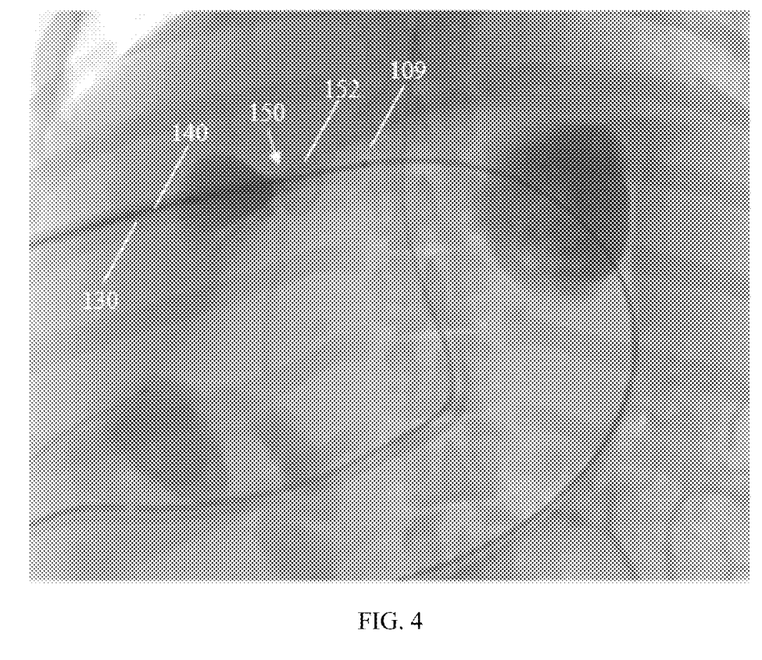
Figure 5:
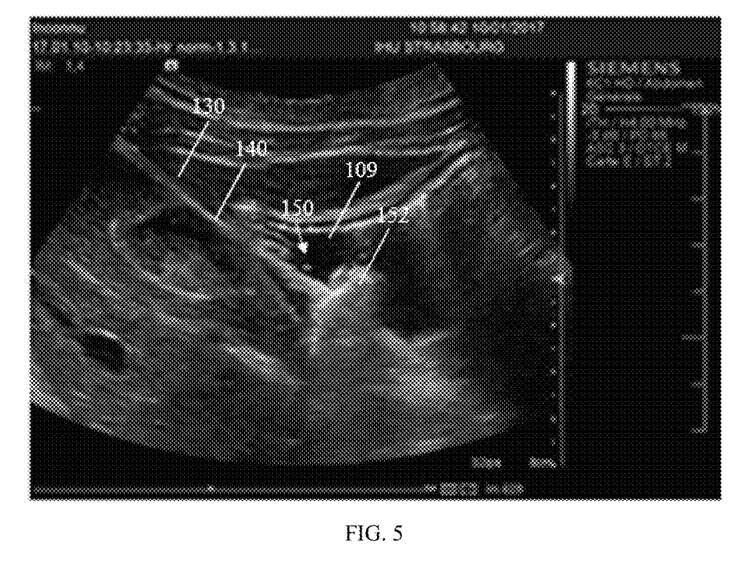

Referring to FIGS. 4-5, the stent delivery system 140 and sheath 130 may be proximally retracted (e.g., pulled) under fluoroscopic (FIG. 4) or ultrasonic (FIG. 5) guidance to place the distal flange 152 of the stent 150 in contact with an inner surface of the stomach 109.

Figure 6A:
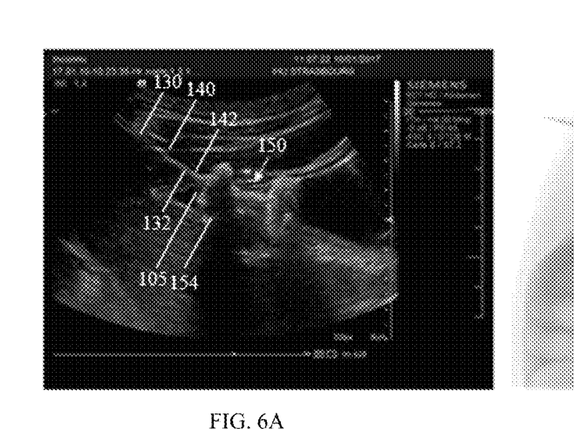
Figure 6B:
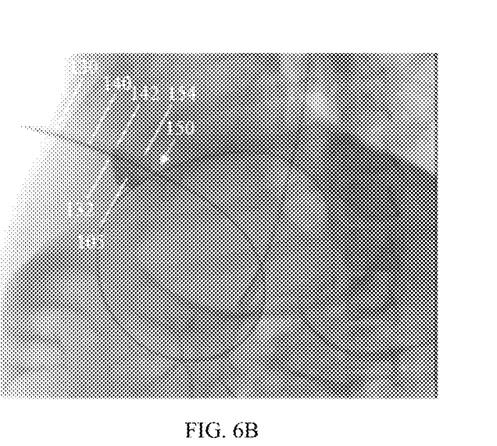

Referring to FIGS. 6A-6B, the sheath 130 and stent delivery system 140 may be further proximally retracted under ultrasonic (FIG. 6A) and/or fluoroscopic (FIG. 6B) guidance to position their respective distal ends 132, 142 within the gallbladder 105. In one embodiment, a biologically inert fluid (e.g., water, normal saline, dextrose 5% water, etc.) may be injected into the gallbladder 105 through the sheath 130 to distend the gallbladder and/or provide an improved ultrasonic image. Still using ultrasonic and/or fluoroscopic guidance, a proximal portion of the drainage stent 150 may be exposed from within stent delivery system 140, such that the proximal portion forms a proximal flange 154 of the stent 150 within the gallbladder 105, thereby providing an open flow path or access path between the gallbladder and stomach.

Figure 7:
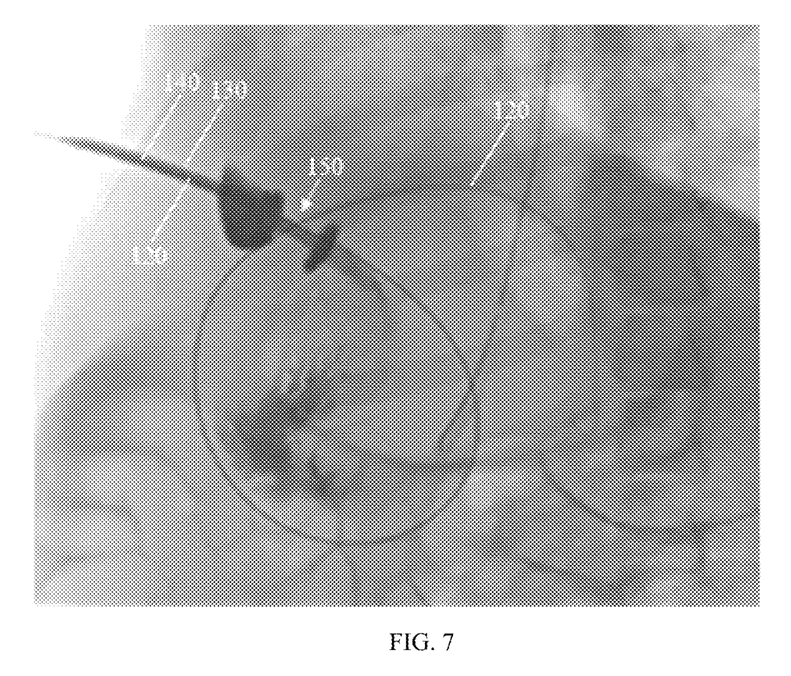

Referring to FIG. 7, with the drainage stent 150 properly deployed, the stent delivery system 140 may be removed over the guidewire 120 and through the sheath 130. The sheath and guidewire may then also be removed from the patient. Depending on the individual patient's post-operative health (e.g., if the gallbladder drainage procedure has alleviated all or some of their symptoms), the drainage stent may be removed after approximately 4-6 weeks by an EUS procedure, or under direct visualization (e.g., through an endoscope, gastroscope, or duodenal scope, etc.).

In certain medical procedures, the stomach may represent the preferred lumen for gallbladder drainage due to the relatively robust nature of the gastric wall. For example, the gastric wall may resist abrasion or perforations caused by contact with the drainage stent, and/or be more amenable to receiving sutures or staples to close the anastomosis following removal of the drainage stent. In certain other medical procedures, the duodenum may represent the preferred lumen for gallbladder drainage. For example, although the tissue wall of the duodenum tends to be less robust than the gastric wall, the shorter distance between the gallbladder and duodenum may allow the deployed drainage stent to exert less force on or between the tissue walls. Pre-procedure imaging of the patient's anatomy may be used to identify the optimal route (e.g., most direct and/or unobstructed pathway) for the medical procedure. A percutaneous cholecystoduodenostomy procedure may involve placing a drainage stent between the gallbladder (e.g., second body lumen) and duodenum (e.g., first body lumen) by following the same steps as those outlined above, with the exception that the needle 110 of FIGS. 2A and 2B, is advanced from the gallbladder at an angle that bypasses the gastric wall and penetrates the duodenal wall (e.g., first tissue wall) and into the duodenum (not shown). Alternatively, a percutaneous cholecystojejunostomy procedure may involve placing a drainage stent between the gallbladder (e.g., second body lumen) and jejunum (e.g., first body lumen) by following the same steps as those outlined above, with the exception that the needle 110 of FIGS. 2A and 2B, is advanced from the gallbladder at an angle that bypasses the gastric wall and penetrates the jejunum wall (e.g., first tissue wall) and into the jejunum (not shown).

A percutaneous gastroduodenostomy procedure may involve placing a drainage stent between the stomach (e.g., second body lumen) and duodenum (e.g., first body lumen) by advancing a needle through a portion of the peritoneal cavity prior to penetrating the stomach, and further advancing the needle through the duodenum wall (e.g., first tissue wall) and into the duodenum (e.g., first body lumen).

A percutaneous gastrojejunostomy procedure may involve placing a drainage stent between the stomach (e.g., second body lumen) and jejunum (e.g., first body lumen) by advancing a needle through a portion of the peritoneal cavity prior to penetrating the stomach, and further advancing the needle through the jejunum wall (e.g., first tissue wall) and into the jejunum (e.g., first body lumen).

A percutaneous gastroileostomy procedure may involve placing a drainage stent between the stomach (e.g., second body lumen) and ileum (e.g., first body lumen) by advancing a needle through a portion of the peritoneal cavity prior to penetrating the stomach, and further advancing the needle through the ileum wall (e.g., first tissue wall) and into the ileum (e.g., first body lumen).

A percutaneous choledochoduodenostomy procedure may involve placing a drainage stent between the common biliary duct (e.g., second body lumen) and duodenum (e.g., first body lumen) by advancing a needle through a portion of the peritoneal cavity prior to penetrating the common biliary duct, and further advancing the needle through the duodenum wall (e.g., first tissue wall) and into the duodenum (e.g., first body lumen).

A percutaneous enteroenterostomy procedure may involve placing a drainage stent between a first portion of the intestine (e.g., second body lumen) and a second portion of the intestine (e.g., first body lumen) by advancing a needle through a portion of the peritoneal cavity prior to penetrating the first portion of the intestine, and further advancing the needle through the intestine wall (e.g., first tissue wall) and into the second portion of the intestine (e.g., first body lumen).

A percutaneous pseudocyst (e.g., walled-off pancreatic necrosis (WOPN), pancreatic fluid collection, etc.) or abscess procedure may involve placing a drainage stent between the pseudocyst or abscess (e.g., second body lumen) and duodenum or stomach (e.g., first body lumen) by advancing a needle through a portion of the peritoneal cavity prior to penetrating the pseudocyst or abscess, and further advancing the needle through the duodenum or stomach wall (e.g., first tissue wall) and into the second portion of the duodenum or stomach (e.g., first body lumen).

A percutaneous external biliary drain conversion procedure may involve placing a drainage stent between the gallbladder and stomach or duodenum, as described above. The biliary duct (e.g., common bile duct) may then be routed through the existing needle tract from the gallbladder to the skin to drain externally (e.g., into a collection bag).

Although the systems and methods of the present disclosure include a combination of ultrasonic and/or fluoroscopic imaging modalities, in various embodiments, the methods disclosed herein may be performed using only ultrasonic imaging. For example, certain patients may not be indicated for radiology procedures or are too sick to be transferred to the radiology department. Alternatively, the medical institution may not be fully equipped or staffed to support the fluoroscopy procedure.

The stent configuration depicted in FIGS. 3-7 is provided by way of non-limiting example, and may include a variety of different shapes, configurations, orientations, dimensions and/or materials as required to provide a flow pathway between first and second body lumens, and in some examples, appose adjacent tissue walls.

For example, stents for use with methods in various embodiments of the present disclosure may be self-expanding or balloon-expandable. The stents may be formed from a suitable polymeric or metallic material. In one embodiment, upon release from constraint within a stent delivery system, proximal and distal flanges may contact the respective inner surfaces of the first (e.g., gallbladder) and second (e.g., stomach) body lumens to place the tissue walls in apposition along a foreshortened saddle region that extends between the flanges of the stent. In another embodiment, the saddle region between the proximal and distal flanges may not foreshorten, thereby maintaining a gap or space between the first and second body lumens.

A porcine model was employed to test the safety and feasibility of performing an image guided, fully percutaneous, internal gallbladder drainage procedure (e.g., cholecysto-enteric anastomosis) via endoscopic ultrasound guided placement of a fully covered drainage stent. The experimental procedures were performed on seven 30 kg female white pigs under general anesthesia and endotracheal intubation. A percutaneous through-and-through puncture of the gallbladder and into the stomach was performed using an 18-gauge needle under ultrasound and fluoroscopic guidance. A guidewire was then inserted through the lumen of the needle into the stomach, and a 12 Fr sheath was inserted over the guidewire into the gastric lumen. A 10 mm lumen apposing stent (e.g., AXIOS™ stent, Boston Scientific, Marlborough, Mass.) was then percutaneously delivered over the wire and through the sheath. The sheath was retracted under fluoroscopic and ultrasound visualization, to deploy the distal flange of the stent within the stomach and the proximal flange of the stent within the gallbladder. Contrast was then injected to confirm adequate placement of the stent and evaluate post-implantation leakage. Contrast injection demonstrated free flow through the stent with no cholecysto-enteric anastomotic leakage. All materials (e.g., the needle, sheath, guidewire, etc.) were then removed and the cholecysto-enteric anastomosis was examined endoscopically and laparoscopically. A subsequent necropsy of each animal confirmed appropriate stent position and good apposition of the gallbladder and stomach, without injury to surrounding structures. The technical success of each procedure was 100%, with procedure times progressively decreasing for subsequent procedures (e.g., 43 minutes, 27 minutes, 21 minutes, 18 minutes, 22 minutes and 20 minutes). This experiment demonstrates the feasibility and safety of an image guided, fully percutaneous, internal gallbladder drainage procedure, in accordance with embodiments of the present disclosure, as a therapeutic option, e.g., in high risk patients, such as patients with acute cholecystitis. The techniques according to embodiments of the present disclosure, including as described with respect to the experiment, may represent an alternative to both endoscopic ultrasound guided stent placement and/or external percutaneous cholecystostomy tube drainage.

Variations on these devices and other devices, and associated components and features which may be suitable for the systems and methods of the present disclosure, can be found in U.S. application Ser. Nos. 14/186,994, 11/867,636 (issued as U.S. Pat. No. 8,425,539), Ser. No. 12/427,215 (issued as U.S. Pat. No. 8,454,632) and Ser. No. 12/772,762 (issued as U.S. Pat. No. 8,357,193), the entire disclosures of which are herein incorporated by reference in their entirety.

Figure 8A:
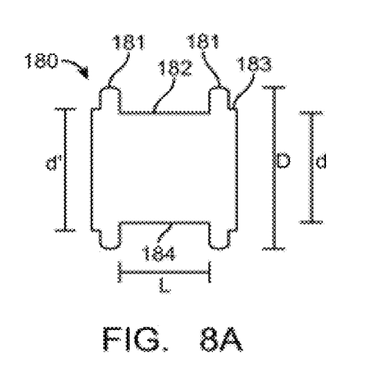
FIGS. 8A-8D illustrate cross-sections of exemplary stents for use in methods, according to embodiments of the present disclosure.
Figure 8B:
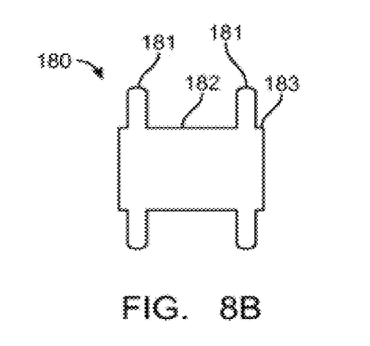
Figure 8C:
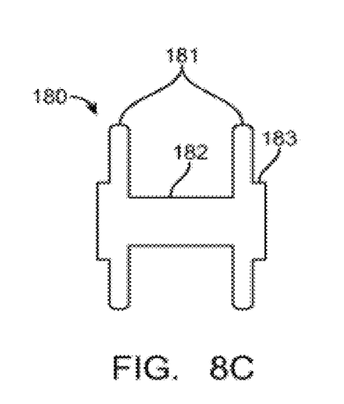

For example, the stent structures shown in FIGS. 8A-8D may be referred to as double-walled flange structures. FIG. 8A illustrates a stent 180 with cylindrical saddle region 182 and a proximal and distal flange 181 with a relatively large diameter open cylindrical region and a wide double cuff or lip 183 on the flange structures 181. FIG. 8B illustrates a stent 180 with a smaller internal diameter than FIG. 8A but with a larger diameter double-walled flange 181 for atraumatically engaging the tissue. FIG. 8C illustrates a stent 180 with an outer cuff or lip 183 diameter that is greater than the diameter of the internal cylindrical saddle region.

Figure 8D:
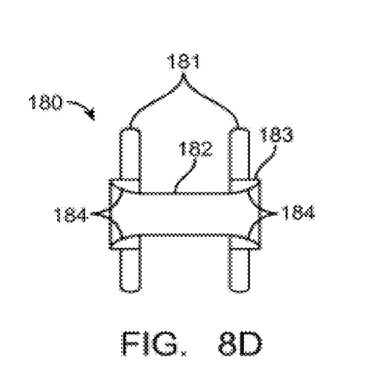

FIG. 8D illustrates an embodiment of a stent 180 similar to FIG. 8C but with a separate plug 184 in the flanges 181 to prevent food, fluids or other materials from getting stuck in the flange volume. The plug may be made of a material that is suitable to flow or pass through the digestive track after the stent is removed. In some embodiments, the flange may be made of a biodegradable or bioabsorbable material. The flange plug structure can be used with any of the stent structures disclosed herein.

In some embodiments, the stent ends are symmetrical. In some embodiments, the stent ends can have different end shapes. The stent end shapes can be selected based on the body lumens and location of the anastomosis and desired physical properties. The stents can be designed to facilitate unidirectional flow, e.g., if food or partially digested food, or fluid or other material are intended to primarily flow in one direction. The unidirectional flow can also exert or require additional strength for the leading stent flange (e.g., proximal flange) that first contacts the flow of material. The proximal flange can be designed with a cross-section that has a stronger pull-out force than the distal flange. The diameter of the opening in the proximal flange can have a wider design than the distal flange to minimize the chances of material getting stuck within the flange. The ends of the proximal flange can also be designed to further decrease the chances of getting food, fluid or other material stuck in the flange. For example, a stent could have the cross-section illustrated in FIG. 10A for the proximal flange with its wider flange end and a flange design like FIG. 10I for the distal flange as illustrated in FIG. 10J, as shown below.

The dimensions of stents for use in various embodiments can be designed to provide a desired hold on the tissue walls along with a desired conduit for fluid flow. For example, the width and diameter of a flange can be optimized to provide the desired properties. A cuff or lip can be provided distally to a flange to provide additional strength. The diameter and length of a cuff can also be optimized to modify the properties of stents. The diameter of a cuff can be greater than the diameter of the cylindrical hollow portion. This can make subsequent access to a stent easier and decrease the chance of material getting stuck in the flange. The cuff or outer lip can also be shaped to minimize the chance of food, partially digested food, or other materials getting stuck within the flange volume. For example, an outer cuff or lip can include a wall that projects or curls away from the interior volume of the stent.

The diameter and length of a stent's cylindrical portion (sometimes referred to as saddle region) can be optimized based on the thickness of the tissue walls and desired stent location. The overall length of stents can also be optimized based on the specific application. The second and third flanges may be separated by a third distance, the third distance being greater than the first distance. The flanges may include an outer diameter $d_1$ that is greater than an outer diameter $d_2$ of the saddle region. For example, outer diameter $d_1$ may be approximately 7.0 mm to approximately 30 mm, and outer diameter $d_2$ may be approximately 3.0 mm to approximately 15.0 mm. For example, in one or more embodiments, the flanges may include an outer diameter $d_1$ that is as much as 75%-100% greater than an outer diameter $d_2$ of the cylindrical saddle region.

Examples of manufacturing techniques for stents include using laser cutting, weaving, welding, etching, and wire forming. A membrane, coating or covering material such as silicone can be applied to an inner or outer surface of the wire stent frame to prevent the passage of fluid through the stent walls. The covering or coating may fully or partially cover a stent frame. The membrane material can be applied by painting, brushing, spraying, dipping, or molding.

Although the flanges of FIGS. 8A-8D are depicted as extending substantially perpendicular to the longitudinal axis of the cylindrical saddle region, in various embodiments one, or both, of these flanges may extend outward towards an end of the elongate body, back towards a center portion of the elongate body, or change directions in some combination of both at points of inflection along the flange as you move from the longitudinal axis to the ends of the flanges. The use of the term "flange" and terms to describe the orientation of flanges with respect to the longitudinal axis of a stent, are not intended to be limiting. For example, a flange may be said to extend, project, protrude, flare, point, or otherwise have an orientation at some degree of angle from the longitudinal axis of a stent.

For example, an end or flange shape can be optimized to improve the strength of a stent and to provide a sufficient amount of linear force apposing and/or opposing each tissue plane while allowing smooth flow of material through the inner lumen opening of saddle regions. End shapes can be described as "bell-like," consisting of multiple structural folds, having a plurality of inflection points, etc. The inflection point can be considered a point of a curve at which a change in the direction of curvature occurs. Additional ends might be rolled or may protrude retrograde against the tissue plane. Alternate designs might consist of a mouth that is wider than the inner diameter of the device.

Figure 9A:
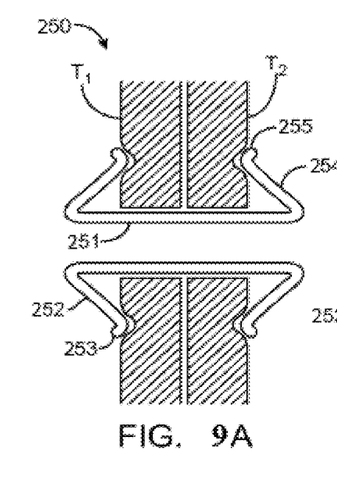
FIGS. 9A-9G illustrate cross-sections of exemplary stents for use in methods, according to embodiments of the present disclosure.
Figures 9B, 9C:
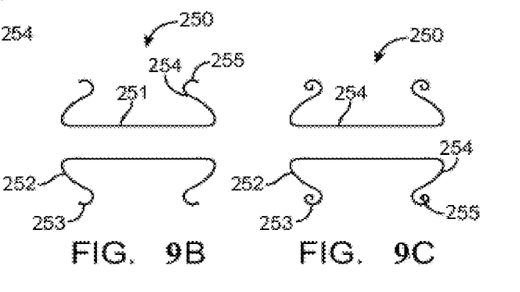

As non-limiting examples of exemplary flange configuration. FIG. 9A illustrates a cross-section of an embodiment of a stent 250 with a cylindrical saddle region 251, flange 252 with an end 253 configured to bend back towards flange 254, flange 254 with an end 255 configured to bend back towards flange 252. The flanges 252, 254 and ends 253, 255 are configured to hold, maintain, or urge the tissue walls T1, T2 in apposition. The distal portion of the flanges 252, 254 are curved to reduce trauma to the tissue walls. FIGS. 9B and 9C have a similar configuration to FIG. 9A but with the ends 253, 255 of the stent further curled or curved. FIG. 9B shows the ends 253, 255 curled or curved in roughly a half circle and FIG. 9C has ends 253, 255 forming approximately a full circle. The ends 253, 255 of the stents in FIGS. 9B-C can atraumatically engage the tissue with increased strength from the additional curling on the distal ends of the stent structure.

Figure 9D:
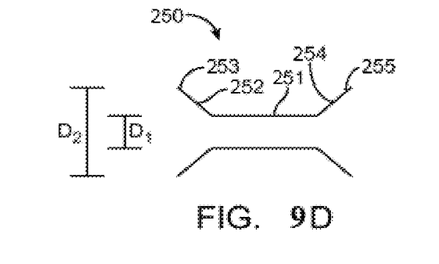
Figure 9E:
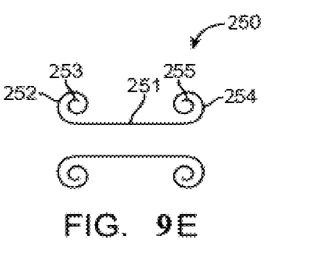
Figure 9F:
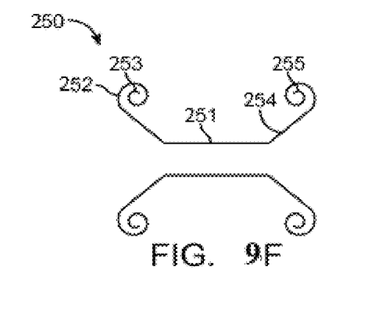
Figure 9G:
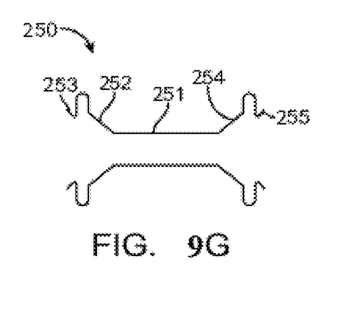

FIGS. 9D-9G illustrate additional cross-sectional views of stent structures. FIG. 9D illustrates a stent 250 with flange structures 252, 254 projecting away from the cylindrical saddle region 251. The cylindrical saddle region 251 has a diameter of D1 and the outer flange structure 252, 254 has a larger diameter D2. FIG. 9E illustrates a stent 250 with flange structures 252, 254 curling or curving outward and away from the interior volume of the cylindrical saddle region 251. FIG. 9F illustrates flange structures 252, 254 that project away from the cylindrical saddle region 251 and have curled or curved ends 253, 255. The curled or curved ends can provide additional lateral strength to the stent. FIG. 9G illustrates flange structures 252, 254 that project away from the interior volume of the cylindrical saddle region 251 and further include double walled flange structures to increase the strength of the stent 250 and to further engage atraumatically with tissue walls when implanted.

FIGS. 10A-10J illustrate a variety of partial cross-sections for stent flange configurations. Some flange structures can have a volume within each flange that might trap food, fluid or other material passing through the stent. The flange can be designed to minimize the chance of food or other material getting trapped within the internal volume of the stent or stent flange. The stents illustrated in FIGS. 10A-10I have flange structures that are designed to minimize food, partially digested food, or other materials getting trapped or stuck within the flange volumes.

Figure 10A:
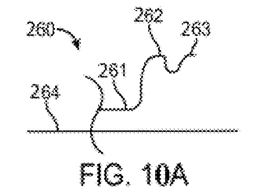
FIGS. 10A-10J illustrate cross-sections of exemplary stents for use in methods, according to embodiments of the present disclosure.

FIG. 10A illustrates a partial cross-section of a stent 260 with a flange structure 262 having a plurality of inflection points. The inflection points create radial bends in the three-dimensional stent structure. The flange 262 wall projects away from the cylindrical saddle region 261 (a first inflection point) then bending back towards the center of the longitudinal pathway 264 of the stent 260 (two more inflection points) followed by bending back again away from the center of the longitudinal pathway 264 of the stent 260 (two more inflection points) and an additional bend at the stent end 263 (one more inflection point). Each of the bends can be considered an inflection point. The stent 260 illustrated in FIG. 10A has 6 inflection points. The inflection points can add additional strength to the stent flange. The stent has an open end with a diameter that is greater than the diameter of the cylindrical saddle region 261 to reduce the likelihood of food, fluids or other materials getting stuck in the stent and to promote the flow of food, partially digested food, fluid and other materials through the stent body. The additional inflection point can increase the lateral strength and pullout force of the expanded stent.

Figure 10B:
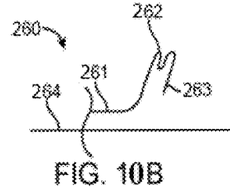

FIG. 10B illustrates a stent 260 with a flange structure 262 having seven inflection points. The structure is similar to the stent illustrated in FIG. 10A but the outer stent wall angles back towards the center of the longitudinal pathway 264 at the end 263.

Figure 10C:
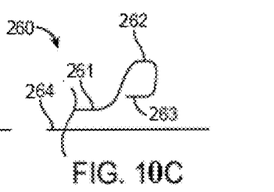

FIG. 10C illustrates a stent 260 with a flange structure 262 including a curled stent end 263. The curled end curls back towards the cylindrical saddle region 261 forming a circular cross-section. The end 263 of the stent flange bends back towards itself so that the fluid flow does not flow directly at the end of the stent. This stent configuration further decreases the likelihood food, fluids or other materials getting stuck within the internal volume of the flange 262.

Figure 10D:
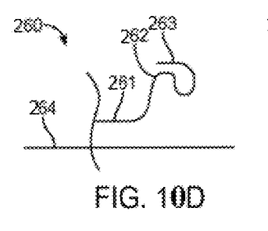

FIG. 10D illustrates a stent 260 with a flange 262 projecting away from the longitudinal pathway 264 of the saddle region 261 and with an end 263 curling or curving outwards past the outer point of the flange 262.

Figure 10E:
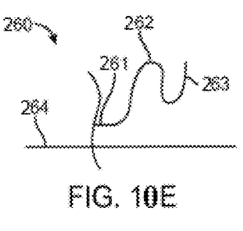

FIG. 10E illustrates a stent 260 with a flange 262 having five inflection points. The flange 262 projects outward away from the center of the saddle region 261 and then bends back towards the center pathway 264 followed by bending again with the end 263 projecting away from the longitudinal center 264 of the cylindrical saddle region 261.

Figure 10F:
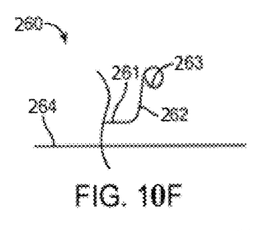

FIG. 10F illustrates a stent 260 with a flange 262 projecting away from the cylindrical saddle region 261 and forming a curled circular cross-section with the end 263 curled or curved back towards the flange 262.

Figure 10G:
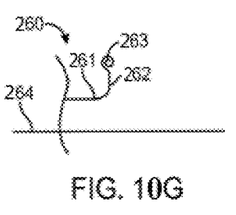

FIG. 10G is similar to FIG. 10F but with the circular end 263 curling or curving to form greater than a full circle at the end 263 of the stent.

Figure 10H:
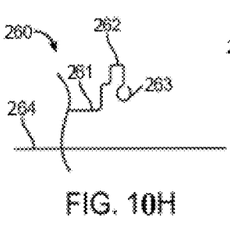

FIG. 10H illustrates a stent flange 262 having multiple bends resembling right angles along with a curled end 263 curling away from the cylindrical center region 261. The right angles can increase the lateral strength and pullout force of the stent.

Figure 10I:
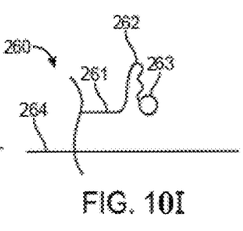
Figure 10J:
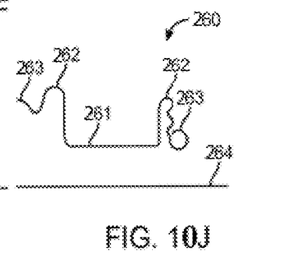

FIG. 10I illustrates a flange having a sinusoidal outer shape with a curled end curling or curving away from the cylindrical saddle region. The wavy sinusoidal outer shape can increase the lateral strength and pullout force of the stent.

FIG. 10J illustrates a stent cross-section one a flange having the structure illustrated in FIG. 10A and a flange illustrates in FIG. 10I. The flange illustrated in FIG. 10A has a wider opened and can be deployed such that it faces the direction of fluid flow. The flange illustrated in FIG. 10I has a narrower outer end and can be used as the opposing end where the material exits the internal volume of the stent.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A method, comprising:
    advancing a hollow needle percutaneously in a direction through a second body lumen and a tissue wall of a first body lumen, such that a distal end of the needle is disposed within the first body lumen;
    advancing a guidewire through the needle into the first body lumen;
    removing the needle from over the guidewire;
    advancing a delivery system for a stent loaded thereon over the guidewire such that a distal end of the delivery system is disposed within the first body lumen; and
    deploying the stent from the delivery system to establish directional fluid flow to the first body lumen from the second body lumen.

2. The method of claim 1, wherein a sheath is advanced over the guidewire such that a distal end of the sheath is disposed within the first body lumen, and wherein the delivery system is loaded over the guidewire and through the sheath.

3. The method of claim 1, wherein the hollow needle comprises a trocar with a sharpened tip and an obturator inserted therethrough, and the obturator is removed from the trocar prior to advancing the guidewire through the trocar.

4. The method of claim 1, wherein the delivery system includes an inner member with a lumen therethrough to receive the guidewire, and an outer member disposed coaxially about the inner member, whereby the stent is loaded on the delivery system between the inner member and the outer member.

5. The method of claim 1, wherein the deploying step comprises exposing a distal portion of the stent from within the delivery system, such that the distal portion forms a distal flange of the stent within the first body lumen.

6. The method of claim 5, wherein the deploying step further comprises retracting the delivery system to place the distal flange of the stent in contact with an inner surface of the tissue wall of the first body lumen.

7. The method of claim 6, wherein the deploying step further comprises retracting the delivery system such that the distal end of the delivery system is disposed within the second body lumen.

8. The method of claim 7, wherein the deploying step further comprises exposing a proximal portion of the stent from within the delivery system, such that the proximal portion forms a proximal flange of the stent within the second body lumen.

9. A method, comprising:
advancing a needle percutaneously to establish an access path in a direction from a second body lumen through a tissue wall of a first body lumen to an interior of the first body lumen;
advancing a guidewire along the access path to the first body lumen interior;
advancing a delivery system for a stent having distal and proximal flanges over the guidewire to the first body lumen interior; and
delivering the stent from the delivery system, such that the distal flange of the stent is deployed in the interior of the first body lumen and the proximal flange of the stent is deployed in the second body lumen, and such that directional fluid flow is established to the first body lumen interior from the second body lumen.

10. The method of claim 9, wherein the distal flange engages a distal face of the tissue wall of the first body lumen and the proximal flange engages an interior wall of the second body lumen.

11. The method of claim 9, wherein after the delivery step the first and second body lumen are apposed and in fluid communication with each other.

12. The method of claim 9, wherein after the delivery step, drainage is established through the stent from the second body lumen to the first body lumen.

13. The method of claim 9, wherein the second body lumen is the gallbladder.

14. The method of claim 9, wherein the tissue wall is the gastric wall and the first body lumen is the stomach.

15. A method, comprising:
establishing a percutaneous directional path of access-to a first body lumen from a second body lumen;
delivering a stent having distal and proximal flanges, when expanded, along the path of access from the second body lumen to the first body lumen;
deploying the distal flange of the stent against a wall of the first body lumen within the first body lumen;
pulling the distal flange back along the path to hold the wall of the first body lumen in apposition to a wall of the second body lumen; and
deploying the proximal flange of the stent against the wall of the second body lumen within the second body lumen, such that directional fluid flow is established to the first body lumen from the second body lumen.

16. The method of claim 15, wherein after the stent is fully deployed drainage is established through the stent from the second body lumen to the first body lumen.

17. The method of claim 15, wherein the first body lumen is the stomach or duodenum and the second body lumen is the gallbladder.

18. The method of claim 15, wherein the percutaneous path passes through a portion of the liver prior to the second body lumen.

19. The method of claim 15, wherein the steps are performed laparoscopically.

20. The method of claim 1, further including injecting a fluid into the first body lumen, the second body lumen, or both, prior to advancing the delivery system.

* * * * *